Figure 1:
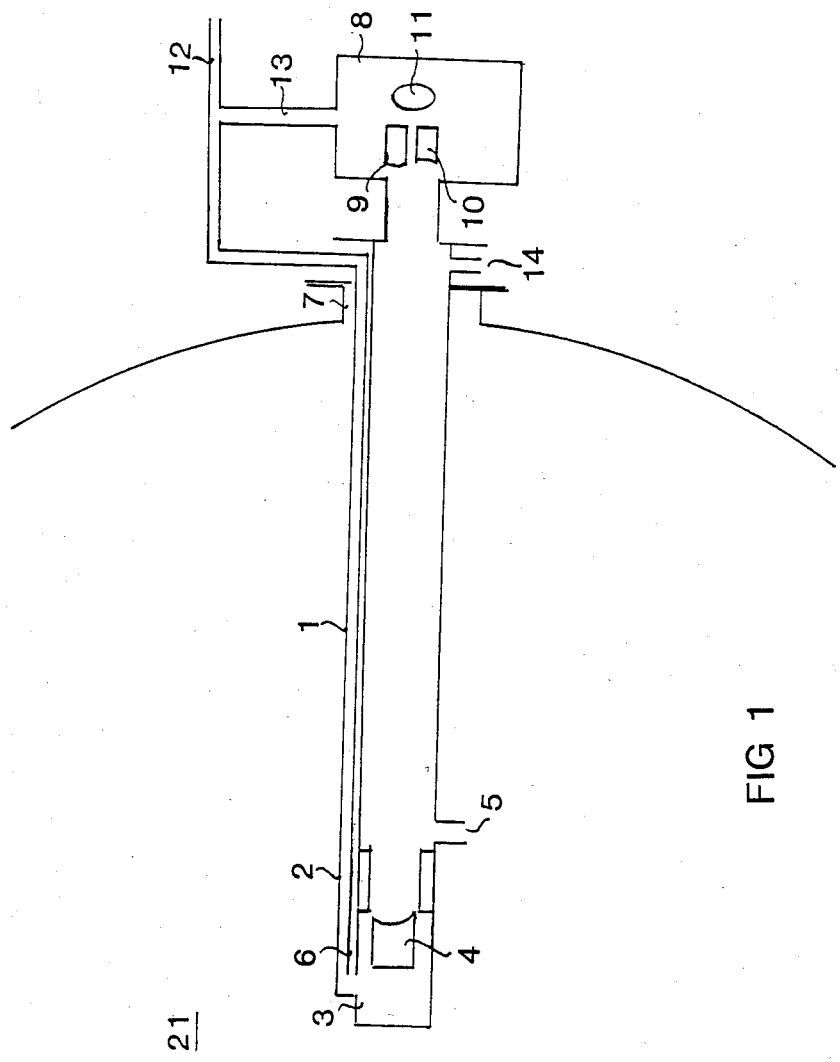

United States Patent [19]

Wennlid

[11] Patent Number: 4,629,704
[45] Date of Patent: Dec. 16, 1986

[54] METHOD FOR ASSAYING SULPHUR TRIOXIDE

[75] Inventor: Sven G. Wennlid, Helsingborg, Sweden

[73] Assignee: Boliden Aktiebolag, Stockholm, Sweden

[21] Appl. No.: 672,255

[22] PCT Filed: Mar. 12, 1984

[86] PCT No.: PCT/SE84/00088
§ 371 Date: Oct. 26, 1984
§ 102(e) Date: Oct. 26, 1984

[87] PCT Pub. No.: WO84/03770
PCT Pub. Date: Sep. 27, 1984

[30] Foreign Application Priority Data

Mar. 18, 1983 [SE] Sweden ................................ 8301488

[51] Int. Cl.⁴ ............................................. G01N 33/00
[52] U.S. Cl. ..................................... 436/119; 436/164
[58] Field of Search ................. 436/119, 122, 164, 39; 356/432, 437–439

[56] References Cited

U.S. PATENT DOCUMENTS

| 2,269,674 | 1/1942 | Liddel et al. | 436/164 |
| 3,489,498 | 1/1970 | Brody et al. | 436/119 |
| 3,553,461 | 1/1971 | Siano et al. | 436/164 |
| 3,712,792 | 1/1973 | Lyshkow | 436/122 |
| 3,945,801 | 3/1976 | Fletcher et al. | 422/98 |
| 4,078,896 | 3/1978 | Moen et al. | 422/91 |
| 4,119,404 | 10/1978 | Price | 436/122 |
| 4,193,963 | 3/1980 | Bruening et al. | 436/122 |
| 4,272,248 | 6/1981 | Neti | 436/122 |
| 4,272,249 | 6/1981 | D'Antonio | 436/136 |
| 4,272,486 | 6/1981 | Harman, III | 436/122 |
| 4,460,544 | 7/1984 | Leichnitz | 436/139 |
| 4,499,190 | 2/1985 | Spicer et al. | 436/122 |

FOREIGN PATENT DOCUMENTS

| 52-69390 | 5/1975 | Japan . | |
| 0204764 | 11/1984 | Japan | 436/119 |
| 1017545 | 1/1966 | United Kingdom | 436/122 |

Primary Examiner—S. Leon Bashore
Assistant Examiner—V. Manoharan
Attorney, Agent, or Firm—Burns, Doane, Swecker & Mathis

[57] ABSTRACT

A method for assaying dry gases comprising sulphur trioxide capable of forming a mist. The gas to be assayed is introduced into a closed space and contacted therein with air comprising normal humidity which reacts with the gas to form a mist, whereafter the light-extinction properties of the mist are measured.

3 Claims, 2 Drawing Figures

METHOD FOR ASSAYING SULPHUR TRIOXIDE

TECHNICAL FIELD

The present invention relates to a method for assaying sulphur trioxide and to apparatus for carrying out the method.

The object of the present invention is to provide a method and apparatus for assaying sulphur trioxide which is capable of forming a mist, and particularly for monitoring industrial emission process gases containing sulphur trioxide, for controlling the recycling of such gases and/or the emission of said gases to the surroundings, with the view of protecting the environment.

BACKGROUND ART

When producing sulphur acid problems relating to the undersirable emission of sulphur trioxide constantly occur, such occurrence being particularly evident when process equipment becomes overloaded and/or break downs in operation occur and/or production is restarted after such break downs.

Such emission can be tolerated in itself, provided that it is on such a small scale as to have no chronic effect on the environment. The emission of such gases must not be continuous, however, and consequently it is necessary to monitor gases which derive from industrial processes and which are liable to create emission problems.

Although with respect to certain gases, it is possible to assay the gas in the actual chimney stack, using light-absorption assaying methods herefor, the gas has either already been discharged from the system to the surroundings, or is in the process of being discharged, thereby rendering it impossible to recycle the gas, should such prove desirable.

Thus, there is a demand for a method by which the sulphur trioxide content of a dry exhaust gas can be measured downstream of an absorption tower in a sulphuric acid plant, so that the gas can be checked and controlled in a rapid fashion.

DISCLOSURE OF THE INVENTION

It has now surprisingly been found possible, in accordance with the present invention, to assay gases containing sulphur trioxide which is able to form a mist, the invention being characterized by drawing the dry gas into a closed space by suction; contacting the gas with air comprising normal humidity which reacts therewith to form a mist; and measuring the light extinction properties of the gas.

By means of the present invention gases comprising sulphur trioxide in an amount down to 35 mg $SO_3$ per $m^3$ can be determined using ordinary air having a normal humidity, i.e. a water content of 15 to 20 g of $H_2O$ per $m^3$. It has been noted that the water content should not be less than about 15 g of $H_2O$ per $m^3$, although the amount of sulphur trioxide is low and that thereby not all water is needed.

Further characterizing features of the invention are set forth in the following claims.

Figure 2:
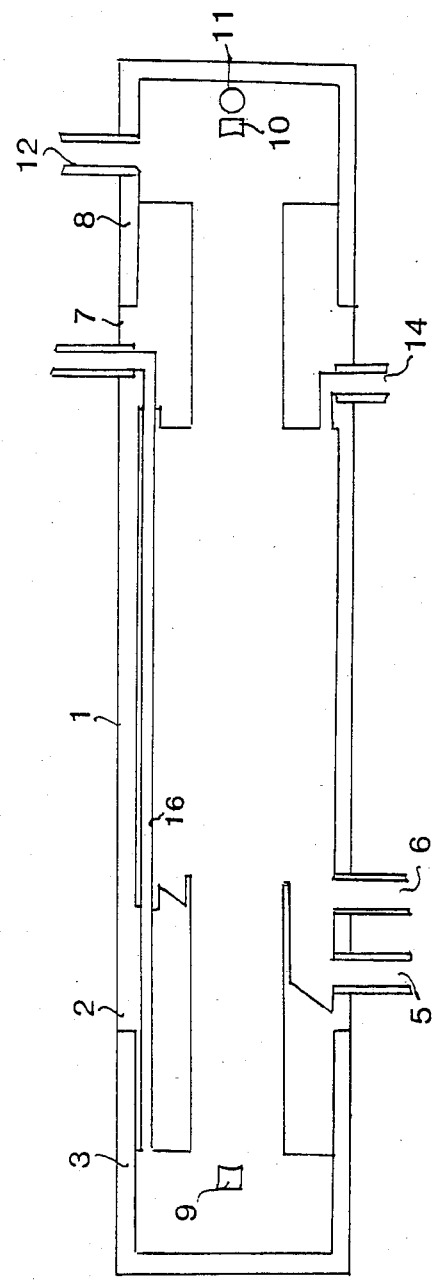

The present invention will now be described with reference to the accompanying drawing, in which FIG. 1 is a sectional view of a preferred first embodiment of an assaying apparatus according to the invention, placed in a residual gas conduit; and FIG. 2 is a cross-sectional view of a second preferred embodiment of an assaying apparatus according to the invention.

Referring first to FIG. 1, there is illustrated a cylindrical tube 1, suitably made of an acid-proof material such as acid-proof steel or polypropylene. Arranged on one end 2 of the tube is a housing 3 which contains a mirror 4. Immediately in front of the housing 3 is a gas inlet pipe 5. Arranged in the vicinity of the mirror 4 is a second inlet pipe 6, said pipe being intended to conduct air and/or an inert gas. Arranged on the other end 7 of the tube 1 is a second housing 8 which contains a photodiode 9 and a receiver, photocell, 10. The receiver 10 is coupled to a transmitter 11, which transfers incoming signals to a writer and/or display instrument (not shown). Coupled to the housing 8 is a supply pipe 12, which is arranged to transfer said air and/or inert gas. The pipe 12 communicates with the pipe 6 and also with a connector 13 arranged around the photodiode 9 and receiver 10, for the introduction of said air/inert gas to the region around said diode and receiver. Also arranged at said other end 7 of the tube 1 is an outlet pipe 14, which is connected to a suction source, for example a vacuum pump (not shown).

The embodiment illustrated in FIG. 2 comprises a cylindrical tube 1, made of polypropylene for example. Arranged at one end 2 of the tube 1 is a housing 3, which accommodates a photodiode 9. The embodiment also includes a pipe 16 through which air for flushing out the interior of the tube can be introduced thereinto. Arranged at the end 2 of the tube 1 are two inlet pipes 5 and 6, the first mentioned pipe being connected to a residual-gas line (not shown) and the latter being connected to an air source. The other end 7 of the tube 1 is provided with a further housing 8, which accommodates a receiver 10 and a transmitter 11. Connected to the housing 8 is a further air-flush inlet pipe 12. Also connected to said other end 7 of the pipe 1 is an outlet pipe 14, which is connected to a suction source not shown.

The apparatus having the following mode of operation:

When using the apparatus illustrated in FIGS. 1–2, the outlet pipe 14 to the vacuum source is opened, whereupon gas is drawn from the residual gas conduit into the tube 1. The gas may comprise a gas leaving an absorption tower in a sulphuric-acid plant, and it is thus desired to measure the residual quantities of sulphur trioxide in the gas. At the same time, moist air is passed through the pipe 6, this air being intended to flush clean the area around the mirror 4 and the photodiode 9 respectively, and to react with any sulphur trioxide present, to form a sulphuric-acid mist. The humidity of the air is that normally present in ambient air under ordinary climate conditions. At the same time as air is drawn in through the pipe 6, air is also drawn in through the piping 12/13 and through the housing 8 so as to flush around the photodiode 9/receiver 10 and the receiver 10 respectively. The photodiode 9 emits a beam of light which, if there is no mist in the tube 1, passes to the receiver 10, at full strenght, optionally via the mirror 4 when the embodiment according to FIG. 1 is used. When a mist is formed, due to presence of sulphur trioxide, the light transmitted is obliterated, either totally or partially, the extent to which said light is blotted being proportional to the amount of sulphur trioxide present.

When the amount of sulphur trioxide present is found to be highly excessive, the gas in the residual gas conduit can be returned to the absorption tower in the sulphuric-acid plant, or can be rendered innocuous in some other way, for example by scrubbing. In the FIG. 2 embodiment it is assumed that a residual gas is introduced through the pipe 5, at the same time as air with normal humidity is drawn in through the pipe 6 and cleaning dry, air is passed through the pipe 16. If any sulphur trioxide is present it will react with the water to form a mist whose ability to extinguish light transmitted from the photodiode can be readily measured in the aforementioned manner.

All gases are withdrawn by suction through the outlet pipe 14, thereby maintaining the light source 9 and receiver 10 free from coatings, for example coatings of sulphuric acid, and continuous assaying can be effected, since fresh gas/gases can constantly be introduced into the apparatus.

By using a mirror/reflector arrangement in accordance with FIG. 1, it is possible to double the length of the light beam, or the instrument can be correspondingly shortened to half its length, such an embodiment being of interest when the apparatus is to be inserted in a residual gas conduit 21. When the tube 1 is also located in the residual gas conduit, it will be heated to the same temperature as the gas, thereby eliminating risk of condensation. Suitably, the interior surfaces of the tube 1 and the houses 3 and 8 are so formed as to prevent any condensate which may form from reaching the light source/receiver units, for example as illustrated in FIG. 2.

When assaying sulphur trioxide, the content range may be 35–1000 mg $SO_3$ per $m^3$ of gas, this range fully covering all current operational conditions.

The above description has been made with reference to gases discharged from process industries. It will be understood, however, that combustion gases can be assayed and controlled in a similar manner, particularly when the combustion gases are substantially free from soot and other particles, as is the case with large combustion plants.

I claim:

1. A method for assaying a gas containing mist-forming sulphur trioxide, comprising drawing the gas to be assayed into a closed space; contracting said gas with air having at least about 15 g of $H_2O$ per $m^3$ which reacts with the sulphur trioxide to form a mist; and measuring the extent to which the mist extinguishes light.

2. The method of claim 1 wherein the gas is introduced into a measuring cell and further gas is passed into a light-measuring unit arranged in the measuring cell.

3. The method of claim 2 wherein the further gas is air, an inert gas or mixtures thereof.

* * * * *